United States Patent [19]
Bridges et al.

[11] Patent Number: 5,879,290
[45] Date of Patent: Mar. 9, 1999

[54] APPARATUS FOR HOLDING INTESTINES OUT OF AN OPERATIVE FIELD

[75] Inventors: Doye R. Bridges, Victoria, Tex.; Jeff S. Schleuning, N. Las Vegas, Nev.

[73] Assignee: BioPlexus Corporation, Las Vegas, Nev.

[21] Appl. No.: 954,252

[22] Filed: Oct. 20, 1997

[51] Int. Cl.$^6$ .................................................. A61B 17/02
[52] U.S. Cl. .......................................... 600/206; 600/210
[58] Field of Search ................................ 600/201, 206, 600/207, 208, 210, 235; 128/850

[56] References Cited

U.S. PATENT DOCUMENTS

| | | | |
|---|---|---|---|
| 1,944,009 | 1/1934 | Homer | 600/206 |
| 2,305,289 | 12/1942 | Coburg . | |
| 3,288,131 | 11/1966 | Garland | 600/206 |
| 3,364,919 | 1/1968 | Hunnicutt | 600/206 |
| 3,863,639 | 2/1975 | Kleaveland | 600/208 X |
| 3,961,629 | 6/1976 | Richter et al. . | |
| 4,533,356 | 8/1985 | Bengmark et al. | 600/206 X |
| 4,848,364 | 7/1989 | Bosman . | |
| 4,889,107 | 12/1989 | Kaufman | 600/206 |
| 5,346,484 | 9/1994 | Van Lindert | 604/358 |
| 5,425,357 | 6/1995 | Moll et al. | 600/207 |
| 5,460,621 | 10/1995 | Gertzman et al. | 604/358 |
| 5,527,264 | 6/1996 | Moll et al. | 600/207 X |
| 5,651,762 | 7/1997 | Bridges | 600/206 |

FOREIGN PATENT DOCUMENTS

| | | | |
|---|---|---|---|
| 787668 | 1/1981 | U.S.S.R. | 600/207 |

Primary Examiner—Jeffrey A. Smith
Attorney, Agent, or Firm—Michael G. Petit

[57] ABSTRACT

A nonabsorbent holding member adapted for use within an abdominal cavity of a patient defined by an anterior wall, a posterior wall and two lateral walls to keep the patient's bowels out of the operative field during open pelvic surgery. The holding member is a substantially U-shaped planar member having a peripheral edge formed of a resiliently deformable material sized to be received within the abdominal cavity. The resilient deformation of at least a portion of the peripheral edge of the holding member results in a residual reactive force against the abdominal cavity to assist in positioning the holding member in the abdominal cavity. The peripheral edge includes a continuous groove lying in the plane of the holding member which circumscribes the elastically deformable peripheral edge to facilitate secure positioning of the holding member within the abdominal cavity.

8 Claims, 3 Drawing Sheets

APPARATUS FOR HOLDING INTESTINES OUT OF AN OPERATIVE FIELD

BACKGROUND OF THE INVENTION

1.) Field of the Invention

The invention relates to apparatus and method for holding intestines out of an operative field. In particular, the invention relates to nonabsorbent bean-shaped surgical holding members, each sized to be received in a patient's abdominal cavity to hold the omentum and intestines out of the operative field during open transabdominal pelvic surgery. An operating procedure for using the holding members is also disclosed.

2.) Description of the Related Art

When pelvic surgery is performed trans-vaginally or with a laparoscope there is generally no delay in return of normal motility to the intestines. However, when open pelvic surgery is required, intra-operative bowel (e.g. intestine and omentum) irritation can result.

Peristalsis is successive waves of involuntary contractions passing along the walls of the intestine forcing the contents onward. The absence or reduction of peristalsis following surgery is referred to as post-operative ileus. Ileus results in bloating, cramping, nausea and vomiting as a result of the mechanical and functional obstruction of the intestines during post-operative recovery. This usually increases a hospital stay by twenty-four to forty-eight hours.

Additionally, during open pelvic surgery the surgeon must be careful while holding the intestines out of the operative field so as not to constrict, or worse, cut off proper flow of the patient's vena cava and aorta that provides blood to and from the heart.

The use of devices for retaining and preventing movement of the viscera, or organs, adjoining the field of an abdominal surgical procedure is common surgical practice. Such retaining devices include pads, such as towels or large sponges, such as a 4 ply-18"×18" disposable laparotomy sponges supplied by Kendell Healthcare Products Company, the Kendell Company, of Mansfield, Mass. These loose woven cloth sponges are used to pack the omentum and the intestines into the abdominal cavity and are often held in place by a metal retractor blade of sufficient width and depth, such as used with the Weinstein retractor device, the "BOOK-WALTER" retractor system, or the O'Sullivan-O'Connor self-retaining abdominal retractor. Both the "BOOK-WALTER" and O'Sullivan-O'Connor retractors are distributed by Codman and Shurtleff, Inc. of Randolph, Mass. The O'Sullivan-O'Connor retractor includes two fixed blades, two removable small blades and one large removable blade.

U.S. Pat. Nos. 4,533,356 and 5,346,484 propose surgical devices for internal use during surgical abdominal operations. However, these two surgical devices, like the pads, are designed to absorb blood and/or wound fluid. It is the inventor's present belief that a nonabsorbent, as compared to an absorbent, holding member reduces irritation and the resultant post-operative ileus.

A disposable abdominal retracting pad known by the trade name DISARP is disclosed in U.S. Pat. No. 4,889,107. This retractor is stated to comprise a flexible flat metal rod having no memory enclosed in urethane plastic foam in turn wrapped in an absorbent woven nylon.

U.S. Pat. No. 4,889,107 further discloses an abdominal retractor that comprises a barrier member forming a surgical dam for retaining viscera in an abdominal cavity during surgery which is stated to be nonabsorbent and is capable of being bent to a selected configuration. A core member made from a soft, malleable aluminum or, alternatively, a metal capable of returning to a predetermined shape after being heated to a certain temperature ("Nitinol") is enclosed within the barrier member to retain the barrier member in a selected configuration. A flexible material such as a plastic foam or silicone rubber encloses the core member and both are covered by a material impermeable to the passage of blood such as silicone rubber, polyvinylchloride or latex.

While U.S. Pat. No. 4,889,107 discloses in FIG. 4 that the side walls and end walls of the barrier member are upright when positioned adjacent to a surgical field in an abdominal cavity, there is no teaching of a fixed presized indentation in the barrier member to provide proper flow through the patient's aorta and vena cava to and from the heart. A fixed presized indentation would relieve the surgeon from physically having to bend the member to a proper configuration. Also, it is believed that the barrier member of U.S. Pat. No. 4,889,107 could bend out of the desired configuration either before or during its use, placing a life threatening constriction on the patient's aorta or vena cava. Further, an indentation in the barrier member of U.S. Pat. No. 4,889,107 was not discussed, disclosed or deemed necessary since the barrier member was not contemplated to be positioned within the walls of the abdominal cavity but, as shown in FIG. 4, the rectangular-shaped barrier member is only placed adjacent to a surgical field with the top and end walls free.

A presized nonabsorbent holding member with a presized or preshaped indentation to allow proper flow of the patient's aorta and vena cava would be desirable. Additionally, an operation procedure whereby the nonabsorbent holding member having a slippery surface that blocks the bowels is positioned between the anterior, lateral and posterior walls of the abdominal cavity would reduce irritation of the bowels and the resultant post-operative discomfort of ileus and shorten the hospital stay while providing a more positive means for holding the bowels out of the operative field during open pelvic surgery.

SUMMARY OF THE INVENTION

A nonabsorbent holding member having a slippery surface adapted for use within a patient's abdominal cavity defined by an anterior wall, a posterior wall and two lateral walls to keep the omentum and intestines out of the operative field during open pelvic surgery is provided. A holding member having a peripheral edge formed of a resiliently deformable foam is presized to be received within the abdominal cavity. The resilient deformation of at least a portion of the peripheral edge of the holding member results in a residual reactive force against the abdominal cavity walls. This residual reactive force assists in positioning of the holding member in the abdominal cavity. Alternatively, the holding member can have a cross section equal or greater than the abdominal cavity to substantially block the intestines in the upper abdomen from the operative field. This blocking or holding of the intestines is achieved while a presized indentation in the holding member allows proper fluid flow to and from the heart via the patient's aorta and vena cava. The plastic foam in the holding member is advantageously formed to protect the aorta and vena cava. The material used for the holding member including the core has a memory when it has a capacity for returning to a former condition or shape independent of external forces, such as, but not limited to, unfolding, uncoiling, unrolling, unbending by the user.

Additionally, a procedure for using the nonabsorbent holding member to assist in holding a portion of the intestines within the abdominal cavity defined by the anterior wall, posterior wall and two lateral walls during the open pelvic operation is provided.

BRIEF DESCRIPTION OF THE DRAWINGS

The object, advantages and features of the invention will become more apparent by reference to the drawings which are appended hereto and wherein like letters or numerals indicate like parts and wherein an illustrative embodiment of the invention is shown, of which.

DETAILED DESCRIPTION OF THE PREFERRED EMBODIMENT

Figure 2:
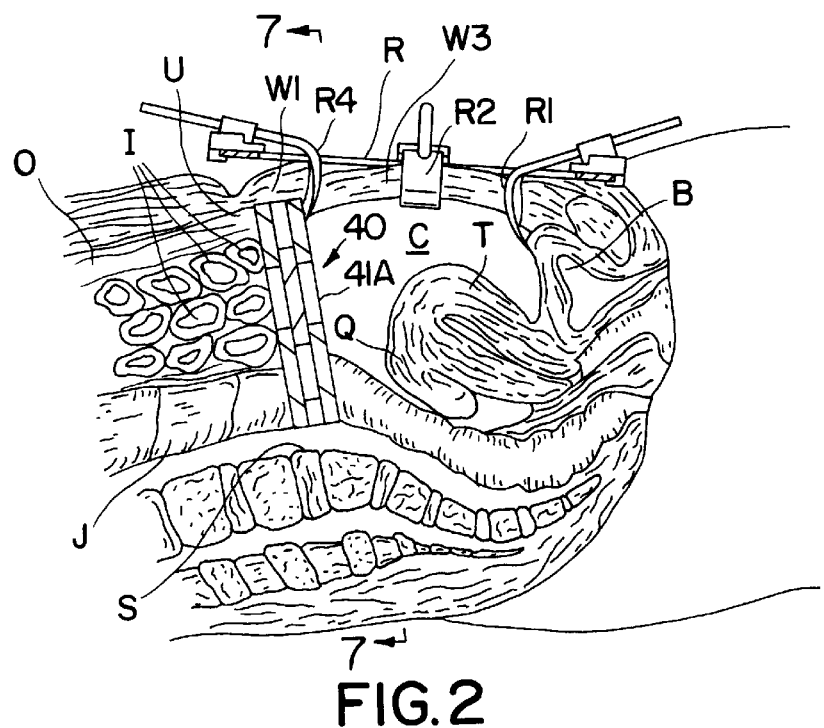
FIG. 2 is an enlarged cross section elevational view of the patient's abdominal cavity with a holding member inserted between the anterior wall adjacent the umbilicus and the posterior wall around a patient's vena cava and aorta.
Figure 4:
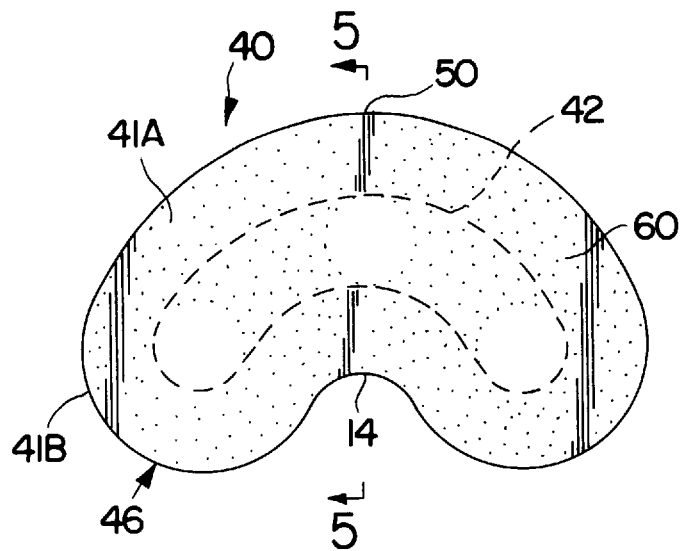
FIG. 4 is a top view of a preferred embodiment of the holding member of the present invention.

The preferred embodiment of the holding member, generally indicated at 40 in FIG. 4 is sized to be received within the abdominal cavity C of a patient P defined by an anterior wall $W_1$, a posterior wall $W_2$, lateral wall $W_3$ and lateral wall $W_4$, as generally shown in FIGS. 2 and 4. The holding member 40 is preferably constructed of two identical sheets of a coated plastic foam sheeting completely sandwiching a foam core, as will be described below in detail.

With reference again to FIG. 4, the plastic foam holding member 40 is generally bean-shaped in top view having an overall curved configuration including an indentation 14. A preferred medium sized holding member 40 would include the center height from the top 50 of the indentation 14 to the top of the foam holding member 40 of approximately 10 centimeters. The overall length of the holding member 40 along a line tangent to the apex of indentation 14 is approximately 26.0 centimeters. The overall height of the holding member 40 is approximately 16.0 centimeters with a total uniform thickness of approximately 2.7 centimeters. This 16.0 centimeter overall height and 10.0 centimeter actual holding member height provides a 6.0 centimeter clearance from the top of indentation 14 to the bottom of the holding member about the patient's aorta and vena cava. The width of each side sheet 41A and 41B overlying and underlying the core 42 (shown in phantom in FIG. 4) is 4.5 centimeters. The core 42 is preferably cut from a cellular silicone foam available from Rogers Corporation of Woodstock, Conn. under the trademark "PORON" S2000 silicone though could be fabricated from other comparable medical grade polymers or materials. Other possible materials that could be used for the holding member could include those disclosed in U.S. Pat. Nos. 2,938,519; 3,863,639; 4,637,377; 4,777,943; 4,889,107 and 4,981,465, which are incorporated by references herein for all purposes.

Returning to FIG. 5, the foam side sheets 41A and 41B are preferably molded from a fairly stiff elastomer, such as a liquid that is injection molded and heat and pressure vulcanized to provide a gum-type material with a memory. Such liquid has been previously supplied as No. 7-6860 by Dow Corning of Midland, Mich. or is now available as Part No. PS1771 by Applied Silicone Corporation of Ventura, Calif.

Figure 5:
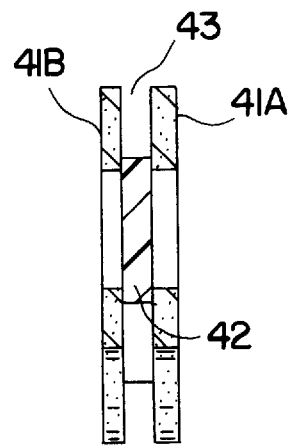
FIG. 5 is a section taken along lines 5—5 of FIG. 4 additionally illustrating the alignment of the sheets and the foam core.
Figure 6:
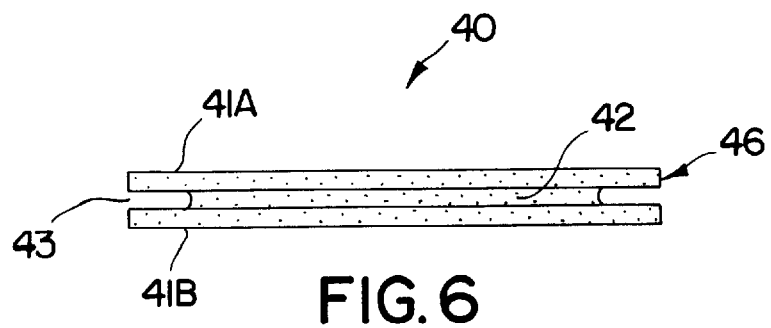
FIG. 6 is a side elevational view of the holding member shown in FIG. 5.

The preferred holding member 40 has an upper or front surface 41A, and a lower or rear surface 41B. The preferred holding member includes a core 42, as best shown in FIGS. 5 and 6, preferably made of a vulcanized silicone elastomer previously available from Dow Corning and now available from Applied Silicone Corporation, as described above. This core is centrally embedded in a cellular silicone foam such as the "PORON" S2000 silicone by Rogers Corporation of Woodstock, Conn. The "PORON" S2000 silicone is a closed cell foam that is nonabsorbent to blood and other body fluids. The foam is cut and provided in two sections 41A, 41B, such as shown in FIGS. 4 and 6. The vulcanized silicone elastomer core 42 is centrally attached to the side foam sections with use of an adhesive, such as the NuSil 1137 adhesive. Preferably, at least 3 centimeters of cellular silicone foam are provided at all points between the peripheral edge of the holding member 40 and the core 42. The other section of the foam siding is then positioned and affixed to the other side of the core by the use of adhesive, to provide an integral one piece holding member. The holding member should then be allowed to cure for 24 hours, trimmed of excess adhesive and cleaned with isopropyl alcohol.

In the preferred embodiment, once the two sections of the foam 41A and 41B are joined by the adhesive with the core 42 therebetween, the holding member 40 may then be completely dip coated, as described above, with a nonabsorbent coating. Preferably, the coating is Part No. 40,000 a medical grade dimethyl silicone elastomer by Applied Silicone Corporation of Ventura, Calif. While the holding member would be nonabsorbent without the coating because of the use of a closed cell foam, the coating is preferred to insure the nonabsorbency and to provide the preferred slippery surface of the holding member 40. While the front surface 41A and the rear surface 41B of the foam cut from the sheet will have a smooth surface, the peripheral edge will have a rougher surface because of the foam cells. Upon coating, the front surface 41A and the rear surface 41B will become more slippery and the edge will still have a sufficiently rough surface to provide good engagement with the abdominal cavity walls.

A preferred medium size holding member 40 would include a center height from the top of the indentation 14 to the top of the holding member 40 (at 50) of approximately 10.0 centimeters. The overall length of the holding member 40 at the tangential intersection at 48 is approximately 26.0 centimeters. The overall height of the holding member 40 is approximately 16.0 centimeters with a thickness of approximately 2.7 centimeters. This 16.0 centimeter overall height and 10.0 centimeter actual holding to member height provides 6.0 centimeters between the indentation to the bottom of the holding member about the patient's aorta and vena cava.

While holding member 40, as shown in FIGS. 4–8, has the same general beanshaped configuration, the holding member 40 has squared off peripheral edge 46. Holding member 40 may have a radiused or curved peripheral edge 46. However, it is to be understood that the holding member 40 could be fabricated with a radiused, curved, combination radiused and flat peripheral edge or other geometric combination edge.

PROCEDURE FOR USE

Turning now to FIGS. 1–3 and 7, the procedure for use of the holding member is shown. During open pelvic surgery, a number of different presized holding members in individual sterile packages will preferably be available to the surgeon. For example, aged patients and smaller patients would use a different sized holding member than that described above for a medium sized patient. However, the overall configurations of these different size holding members can be predetermined by averaging a number of Computerized Axial Tomography (CAT) scan cross sections on the abdominal cavity.

Figure 3:
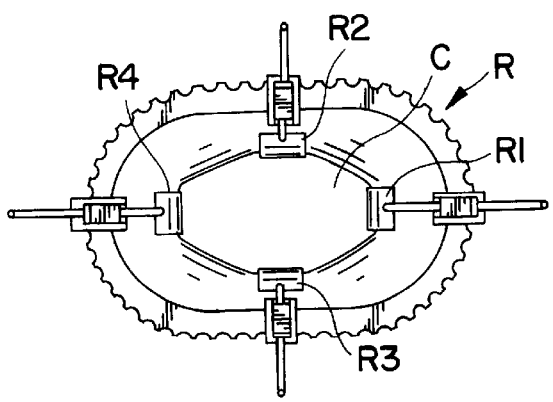
FIG. 3 is a top view of a conventional four-way retractor positioned on the patient as shown in FIGS. 1 and 2.

As best shown in FIGS. 2 and 3, an incision is used to open the pelvic area of the patient P. A lower midline incision, lower transverse incision or any other medically acceptable opening may be used. After retracting the lateral abdominal walls $W_3$ and $W_4$ with blades $R_2$ and $R_3$, respectively, using a conventional 4-way retractor, such as the "BOOKWALTER" retractor R, as shown in FIGS. 1–3 and 7, the urinary bladder B is retracted with a suitably sized lower retractor blade $R_1$. The vertical distance between the sacral spine S and the umbilicus U or anterior wall $W_1$ adjacent the umbilicus U is then measured. This measurement is used to select the proper size holding member.

Figure 1:
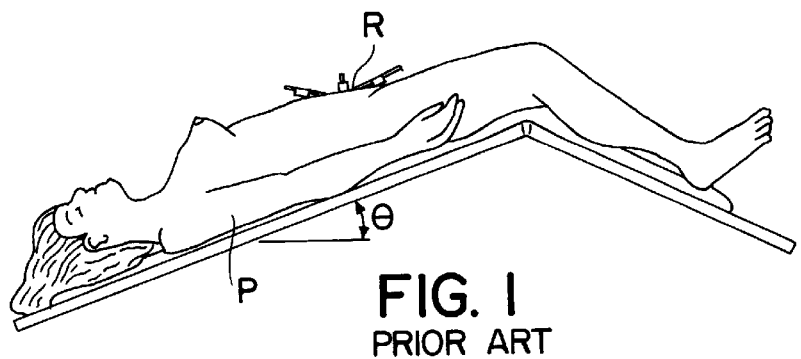
FIG. 1 is an elevational view of the positioning of a conventional retractor on a patient positioned in the "Trendelenburg" position before a holding member of the present invention is inserted in the abdominal cavity.
Figure 7:
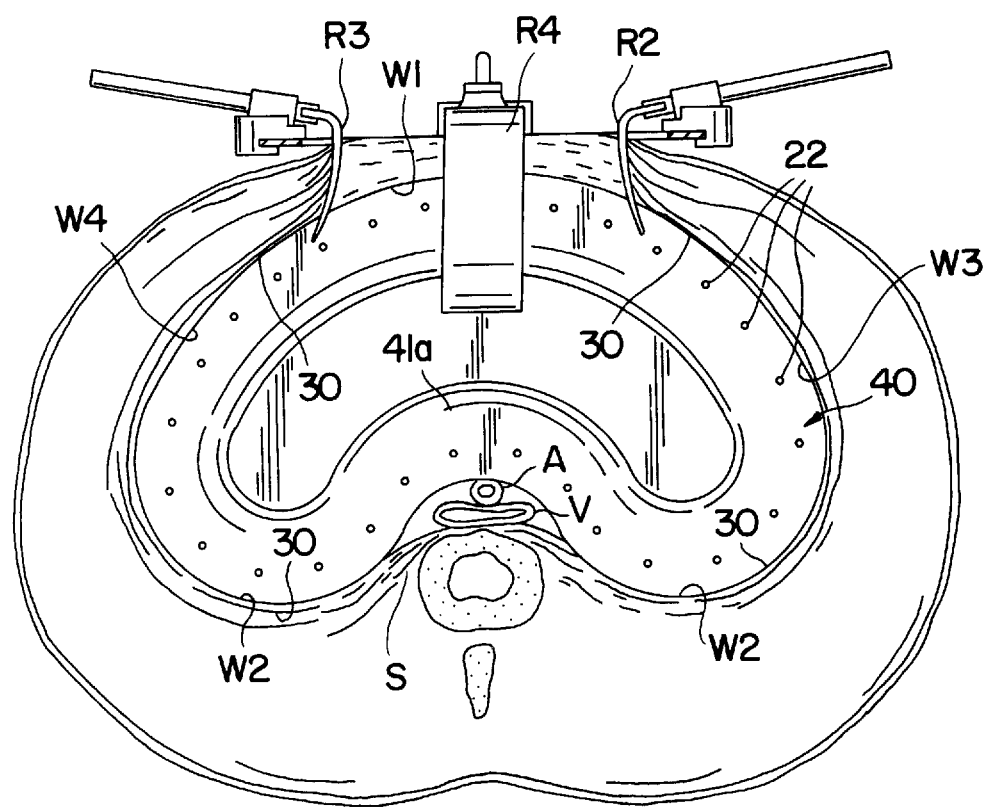
FIG. 7 is an enlarged section view taken along lines 7—7 of FIG. 2 better illustrating the positioning of a holding member of the present invention between the abdominal cavity wall.

Prior to insertion of the holding member, the patient P is placed momentarily into an extreme "Trendelenburg" position allowing the intestines I and omentum O along with the colon J to recede into the upper abdomen as much as possible. FIG. 1 illustrates the basic "Trendelenburg" position, though the angle θ could be larger as desired by the surgeon. The holding member is then moved through the incision into the abdominal cavity C. If desired, using the concave portion of the holding member 40 as a scoop or ii the front surface 41A of the holding member 40, the intestines I are moved further upwards in the upper abdomen until the member is positioned at or preferably 2 centimeters below the umbilicus U. The rear surface 41B of the holding member 40, as best shown in FIG. 2, is concave to centrally locate the intestines. As best shown in FIG. 7, the front surface of the holding member could include a plurality of holes to allow air to vent to and from the holding member, if desired. Even though the holding member is vented, it would still be nonabsorbent if a nonabsorbent material is used for the holding member, such as a closed cell foam.

The holding member 40 will preferably have a cross section of an additional 2 centimeters of foam in all directions than the actual average relaxed abdominal cavity measurements, except, of course, at the indentation 14. This additional material will allow for compression and variations of cavity contours and sizes.

The anterior and lateral abdominal walls of an average patient can withstand considerable pressure from the inside or tension loading during surgery. However, as best shown in FIG. 7, the patient's aorta A and vena cava V above the spine S in the center of the posterior wall $W_2$ should be protected from more than about 15 millimeters mercury pressure. Since the core 42 of the holding member 40 is constructed of a more rigid elastomer, such as the vulcanized silicone elastomer described above, the holding member will transmit pressure to all the abdominal walls W. This core however should not come into contact with the aorta A and vena cava V. Of course, the density of the foam increases as the foam is compressed to the core. In the holding member 40 as the foam is compressed, a denser foam is adjacent the exposed core to protect the aorta A and vena cava V.

After the holding member has been inserted, which should only take 1 or 2 minutes, the patient P is repositioned to a more supine or horizontal position to reduce pressure on the patient's diaphragm. As a precaution, it is recommended that the patient's pulse be checked in the common iliac arteries after insertion of the holding member and one finger inserted between the patient's aorta and vena cava and the holding member to be sure that pressure on the vena cava is not enough to obstruct flow. As a backup, if there is a reduction in venus return, the anesthetist would observe significant tachycardia.

In the alternative, the holding members as shown in the Figures. can be sized so that minimal or no pressure is exerted on the abdominal walls with the holding member acting merely as a blocking member used in combination with the abdominal cavity walls to keep the intestines out of the operative field.

The fourth or upper blade $R_4$ of the retractor R is then moved into the incision and positioned adjacent the core of the respective holding member to hold the intestines I and omentum O in the upper abdomen clear of the operative field on the uterus T and/or ovary Q.

After completing the intra-abdominal phase of the surgery, the holding member is removed along with the 4-way retractor and the incision is closed in the usual manner.

The foregoing disclosure and description of the invention are illustrative and explanatory thereof, and various changes in the size, shape and materials, as well in the details of the illustrated construction may be made without departing from the spirit of the invention.

What is claimed is:

1. Apparatus adapted for use within an abdominal cavity of a patient, said cavity defined by an anterior wall, a posterior wall and lateral walls, said apparatus comprising:

a U-shaped holding member adapted to be received in the patient's abdominal cavity and having a peripheral edge formed of a resiliently deformable polymer and a core formed from a polymer which has the same or greater rigidity than said resiliently deformable polymer, a resilient deformation of at least a portion of said edge of said holding member resulting in a residual reactive force against the abdominal cavity walls, said residual reactive force thereby assisting in positioning said holding member in the abdominal cavity and having a groove circumscribing said peripheral edge of said holding member.

2. Apparatus of claim 1 wherein said edge is fabricated from foam.

3. Apparatus of claim 1 where said edge of said holding member is sized to extend beyond the cross-section of the patient's relaxed abdominal cavity to enhance said residual reactive force.

4. Apparatus of claim 1 wherein the holding member is coated by a layer of polymer.

5. Apparatus of claim 1 wherein said edge of the holding member is flat.

6. Apparatus of claim 1 wherein said holding member having a presized indentation.

7. Apparatus of claim 6 wherein said indentation is adapted to be positioned about the patient's aorta and vena cava.

8. Apparatus of claim 1 wherein said core is fabricated from a vulcanized silicone elastomer.

* * * * *